United States Patent
Grashow (10) Patent No.: US 11,844,898 B2
(45) Date of Patent: Dec. 19, 2023

(54) SYSTEM AND METHOD FOR DETECTING STROKE IN PATIENTS DURING PRESSURE SUPPORT THERAPY

(71) Applicant: KONINKLIJKE PHILIPS N.V., Eindhoven (NL)

(72) Inventor: Jonathan Sayer Grashow, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1187 days.

(21) Appl. No.: 16/139,659

(22) Filed: Sep. 24, 2018

(65) Prior Publication Data
US 2019/0091426 A1 Mar. 28, 2019

Related U.S. Application Data

(60) Provisional application No. 62/564,646, filed on Sep. 28, 2017.

(51) Int. Cl.
*A61M 16/00* (2006.01)
*A61B 5/00* (2006.01)
(Continued)

(52) U.S. Cl.
CPC .......... *A61M 16/0051* (2013.01); *A61B 5/02* (2013.01); *A61B 5/087* (2013.01); *A61B 5/0826* (2013.01);
(Continued)

(58) Field of Classification Search
CPC ....... A61B 5/0205; A61B 5/7282; A61B 5/72; A61B 5/087; A61B 5/0826; A61B 5/02;
(Continued)

(56) References Cited

U.S. PATENT DOCUMENTS 3,946,729 A * 3/1976 Hanna ...................... A61B 5/08
128/204.23
5,148,802 A 9/1992 Sanders et al.
(Continued)

FOREIGN PATENT DOCUMENTS

CN 102512736 A 6/2012
JP 2006061223 A 3/2006
(Continued)

OTHER PUBLICATIONS

Mohsenin, Obstructive Sleep Apnea: A new preventative and therapeutic target for stroke, 2015, The American Journal of Medicine, pp. 811-816 (Year: 2015).*
(Continued)

*Primary Examiner* — Joseph D. Boecker (57) ABSTRACT

A method of detecting stroke in a patient receiving a pressure support therapy includes: receiving data from one or more sensors structured to gather data related to patient respiration while receiving pressure support therapy from an airflow generator via a patient circuit; analyzing the data from the one or more sensors while pressure support therapy is provided to the patient; determining that the analyzed data from the one or more sensors is indicative of a patient experiencing respiratory changes indicative of a stroke; and responsive to said determining, triggering at least one alarm.

11 Claims, 3 Drawing Sheets

(51) Int. Cl.
*A61B 5/087* (2006.01)
*A61B 5/08* (2006.01)
*A61B 5/02* (2006.01)
*G16H 50/20* (2018.01)
*A61M 16/08* (2006.01)
*A61B 5/1455* (2006.01)
*A61B 5/145* (2006.01)
*A61M 16/20* (2006.01)

(52) U.S. Cl.
CPC .............. *A61B 5/4818* (2013.01); *A61B 5/72* (2013.01); *A61B 5/7282* (2013.01); *A61M 16/00* (2013.01); *A61M 16/0069* (2014.02); *A61M 16/024* (2017.08); *G16H 50/20* (2018.01); *A61B 5/14542* (2013.01); *A61B 5/14551* (2013.01); *A61B 5/6885* (2013.01); *A61B 2505/03* (2013.01); *A61B 2505/05* (2013.01); *A61M 16/0858* (2014.02); *A61M 16/204* (2014.02); *A61M 2016/003* (2013.01); *A61M 2016/0027* (2013.01); *A61M 2016/0039* (2013.01); *A61M 2205/18* (2013.01); *A61M 2205/50* (2013.01); *A61M 2230/205* (2013.01)

(58) Field of Classification Search
CPC .............. A61B 5/4818; A61B 2505/03; A61B 5/14551; A61B 5/6885; A61B 2505/05; A61B 5/14542; A61B 5/0816; A61B 5/0823; A61M 16/0051; A61M 16/00; A61M 16/0069; A61M 16/024; A61M 2016/003; A61M 2205/50; A61M 2205/18; A61M 2230/205; A61M 16/204; A61M 2230/60; A61M 16/203; A61M 2205/15; A61M 2016/0027; A61M 2016/0039; A61M 16/0858; A61M 16/0066; A61M 16/026; G16H 50/20
See application file for complete search history.

(56) References Cited

U.S. PATENT DOCUMENTS

| | | | |
|---|---|---|---|
| 5,313,937 A | | 5/1994 | Zdrojkowski |
| 5,433,193 A | | 7/1995 | Sanders et al. |
| 5,558,086 A | * | 9/1996 | Smith ............... A61M 16/0677 128/204.26 |
| 5,632,269 A | | 5/1997 | Zdrojkowski |
| 5,803,065 A | | 9/1998 | Zdrojkowski et al. |
| 6,029,664 A | | 2/2000 | Zdrojkowski et al. |
| 6,539,940 B2 | | 4/2003 | Zdrojkowski et al. |
| 6,626,175 B2 | | 9/2003 | Jafari et al. |
| 7,011,091 B2 | | 3/2006 | Hill et al. |
| 2002/0185130 A1 | * | 12/2002 | Wright ............... A61M 16/085 600/533 |
| 2006/0037615 A1 | * | 2/2006 | Wilkinson ............ A61B 8/08 128/204.23 |
| 2006/0084877 A1 | * | 4/2006 | Ujhazy ............. A61M 16/0069 600/483 |
| 2008/0257349 A1 | * | 10/2008 | Hedner ................. A61B 5/087 128/204.23 |
| 2010/0006098 A1 | * | 1/2010 | McGinnis ......... A61M 16/0051 128/204.23 |
| 2010/0018530 A1 | * | 1/2010 | Schindhelm ...... A61M 16/0051 128/204.23 |
| 2011/0092839 A1 | * | 4/2011 | Alshaer ................. A61M 16/00 600/529 |
| 2012/0142647 A1 | * | 6/2012 | Dax ....................... A61K 31/57 544/323 |
| 2012/0234332 A1 | * | 9/2012 | Shantha ............... A61N 1/3601 128/848 |
| 2014/0007878 A1 | | 1/2014 | Armitstead et al. |
| 2014/0144431 A1 | | 5/2014 | Darkin et al. |
| 2016/0121072 A1 | * | 5/2016 | Smith ............... A61M 16/0866 128/206.21 |
| 2018/0140252 A1 | | 5/2018 | Luxon |

FOREIGN PATENT DOCUMENTS

| | | | |
|---|---|---|---|
| KR | 20060036974 A | 5/2006 | |
| WO | WO-2005079897 A1 * | 9/2005 | ........... A61B 5/4818 |
| WO | 2017109634 A1 | 6/2017 | |

OTHER PUBLICATIONS

Yaggi, H. et al., "Obstructive Sleep Apnea as a Risk Factor for Stroke and Death", The New England Journal of Medicine, 2005. pp. 2034-2041.
Mims, K., et al., "Sleep and Stroke", Sleep Med Clin, 2015.
Aaronson, J. et al., "The effect of obstructive sleep apnea and treatment with continuous positive airway pressure on stroke rehabilitation: rationale, design and methods of the TOROS study", BMC Neurology 2014, 14:36.
Howard, R. et al., "Pathophysiological and clinical aspects of breathing after stroke", Postgrad Med Journal, 2001, pp. 700-702.
Frank, J. et al., "Respiratory Failure with Cervicomedullary Infarctions", J Stroke Cerebrovasc Dis, 1995, 61-65.
Li-mei, L., "Clinical Observation on Acupuncture plus Auricular Point Sticking Therapy for Post Stroke Hiccups", J. Acupunct. Tuina. Sci. 2012, 10 (5): 310-312.
Culebras, A., "Sleep and Stroke", Seminars in Neurology, vol. 29, No. 04, Sep. 2009.

* cited by examiner

SYSTEM AND METHOD FOR DETECTING STROKE IN PATIENTS DURING PRESSURE SUPPORT THERAPY

CROSS-REFERENCE TO PRIOR APPLICATIONS

This application claims the benefit of U.S. Provisional Application No. 62/564,646, filed on 28 Sep. 2017. This application is hereby incorporated by reference herein.

BACKGROUND OF THE INVENTION

1. Field of the Invention

The present invention pertains to methods of detecting stroke in a patient receiving a pressure support therapy. The present invention also pertains to pressure support devices for carrying out such methods.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

It is well known to treat sleep disordered breathing by applying a positive airway pressure (PAP) to the patient's airway using an airway pressure support system that typically includes a mask, a pressure generating device, and a conduit to deliver positive pressure breathing gas from the pressure generating device to the patient through the mask. This positive pressure effectively "splints" the airway, thereby maintaining an open passage to the lungs. In one type of PAP therapy, known as continuous positive airway pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Stroke events are strongly associated with sleep disordered breathing with an estimated 75% of stroke patients suffering from OSA. Treating sleep disordered breathing has been shown to improve stroke patient outcomes, but patients who have had one or more strokes remain at high risk for subsequent strokes even while on PAP therapy.

The majority of stroke patients who have OSA experience stroke events during the night (while the majority of non-OSA stroke patients experience stroke events in the morning). When a stroke occurs, changes in respiration can be detected in approximately 60% of cases. The specific respiratory changes depend on the region(s) of the brain affected by the stroke lesions. Possible respiratory changes include:
a. Acute respiratory failure
b. Central Hypoventilation Syndrome (Ondine's Curse)
c. Emergence/exacerbation of OSA, CSA, and Cheyne-Stokes
Respiration
d. Neurogenic Hyperventilation
e. Reduced CO2 sensitivity
f. Apneustic Breathing
g. Ataxic Respiration
h. Intractable Hiccups When a stroke event occurs, the time to treatment is critical to improving patient outcomes. In cases of acute respiratory failure or central hypoventilation syndrome, patient death is imminent and mechanical ventilation should be started within minutes. In other cases, where the effects of a stroke event do not result in impairment of critical bodily functions, treatment within three hours is associated with significantly improved patient functional and cognitive outcomes because this timeframe is associated with successful treatment using Tissue Plasminogen Activator (tPA), a medication used to dissolve clots.

SUMMARY OF THE INVENTION

This invention comprises methods to monitor high risk stroke patients for possible strokes using the patient's PAP device so that emergency action can be initiated in a timely fashion.

As one aspect of the invention, a method of detecting stroke in a patient receiving a pressure support therapy is provided. The method comprises: receiving data from one or more sensors structured to gather data related to patient respiration while receiving pressure support therapy from an airflow generator via a patient circuit; analyzing the data from the one or more sensors while pressure support therapy is provided to the patient; determining that the analyzed data from the one or more sensors is indicative of a patient experiencing respiratory changes indicative of a stroke; and responsive to said determining, triggering at least one alarm.

Determining that the analyzed data from the one or more sensors is indicative of a patient experiencing respiratory changes indicative of a stroke may comprise analyzing patient airflow and pressure waveforms.

The one or more sensors may comprise a pressure sensor and a flow sensor.

The method may further comprise determining the patient is a high risk stroke patient prior to receiving data from the one or more sensors.

The method may further comprise, if the analyzed data from the one or more sensors is determined to indicate the patient is experiencing respiratory changes indicative of a stroke, adjusting settings of the airflow generator.

Adjusting settings of the airflow generator may comprise adjusting settings of the airflow generator to provide mandatory life-sustaining ventilation of the patient.

Respiratory changes indicative of a stroke may include at least one of: acute respiratory failure; central hypoventilation syndrome; emergence/exacerbation of OSA, CSA and Cheyne-Stokes Respirastion; neurogenic hyperventilation, reduced $CO_2$ sensitivity; apneustic breathing; ataxic respiration; and intractable hiccups.

Triggering at least one alarm may comprise triggering an audible alarm. Triggering at least one alarm may comprise triggering a visual alarm. Triggering at least one alarm may comprise sending an automated message to at least one of a physician or a caregiver.

Triggering at least one alarm may comprise alerting emergency services.

As another aspect of the invention a pressure support device for providing pressure support therapy to a patient is provided. The pressure support device comprises: an airflow generator structured to generate pressure to provide pressure compensation to the patient via a patient circuit; one or more sensors structured to gather data related to effectiveness of the pressure compensation; and a processing unit programmed to: receive data from the one or more sensors; analyze the data from the one or more sensors while pressure support therapy is provided to the patient; determine that the analyzed data from the one or more sensors is indicative of a patient experiencing respiratory changes indicative of a stroke; and responsive to said determining, trigger at least one alarm.

The one or more sensors may comprise a pressure sensor and a flow sensor.

The pressure support device may further comprise an audible indicator and the processing unit may be programmed to activate the audible indicator responsive to said determining.

The pressure support device may further comprise a visual indicator and the processing unit may be programmed to activate the visual indicator responsive to said determining.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
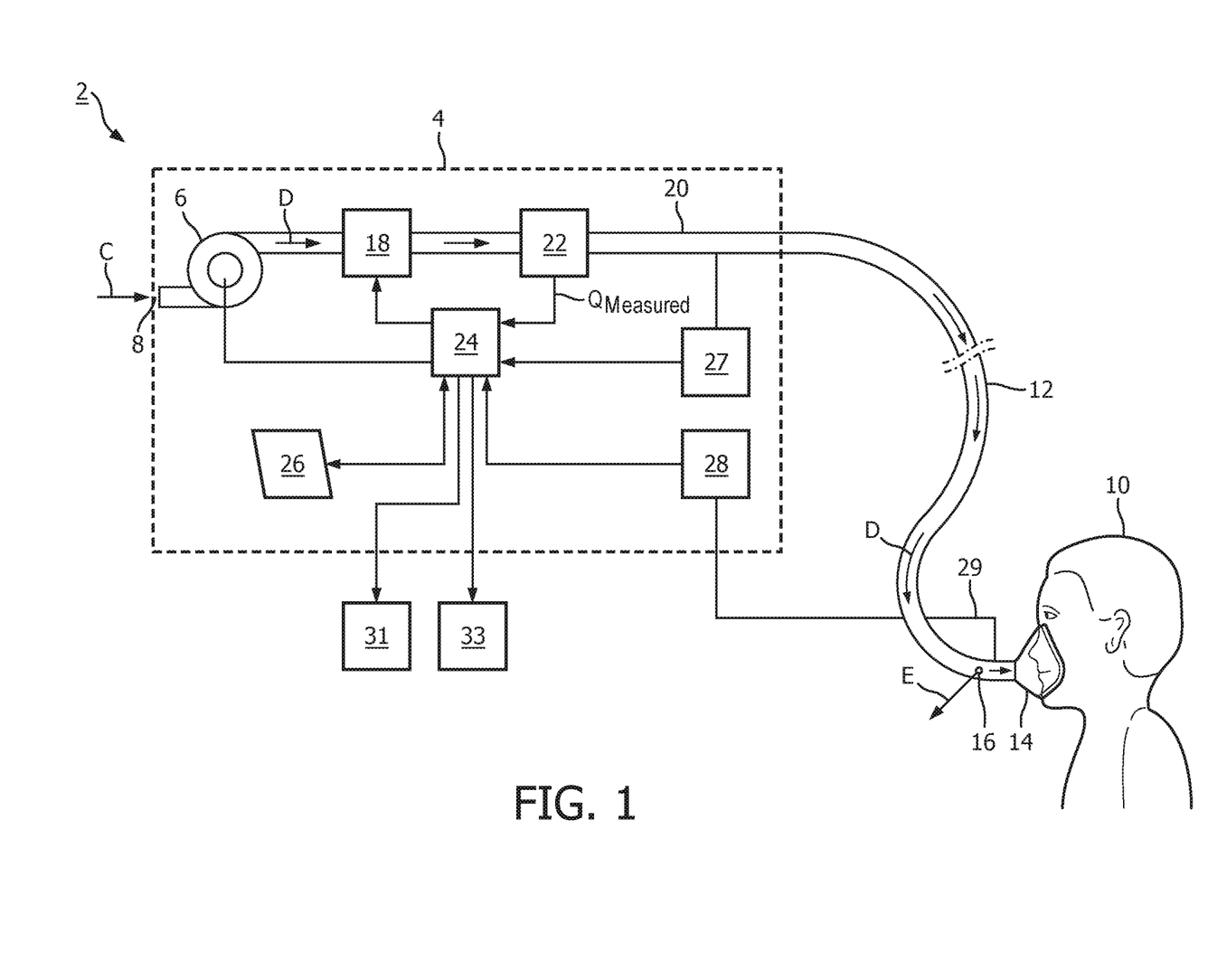
FIG. 1 is a schematic diagram of a pressure support system adapted to provide a regimen of respiratory therapy to a patient according to an exemplary embodiment of the disclosed concept.

FIG. 1 is a schematic diagram of an airway pressure support system 2 according to one particular, non-limiting exemplary embodiment in which the present invention may be implemented. Referring to FIG. 1, airway pressure support system 2 includes a pressure support device 4 which houses a gas flow generator 6, such as a blower used in a conventional CPAP or bi-level pressure support device. Gas flow generator 6 receives breathing gas, generally indicated by arrow C, from the ambient atmosphere through a filtered air inlet 8 (described in greater detail herein) provided as part of pressure support device 4, and generates a flow of breathing gas therefrom for delivery to an airway of a patient 10 at relatively higher and lower pressures, i.e., generally equal to or above ambient atmospheric pressure. In the exemplary embodiment, gas flow generator 6 is capable of providing a flow of breathing gas ranging in pressure from 3-30 cmH2O. The pressurized flow of breathing gas from gas flow generator 6, generally indicated by arrow D, is delivered via a delivery conduit 12 to a breathing mask or patient interface 14 of any known construction, which is typically worn by or otherwise attached to patient 10 to communicate the flow of breathing gas to the airway of patient 10. Delivery conduit 12 and patient interface device 14 are typically collectively referred to as a patient circuit.

Pressure support system 2 shown in FIG. 1 is what is known as a single-limb system, meaning that the patient circuit includes only delivery conduit 12 connecting patient 10 to pressure support system 2. As such, an exhaust vent 16 is provided in delivery conduit 12 for venting exhaled gases from the system as indicated by arrow E. It should be noted that exhaust vent 16 can be provided at other locations in addition to or instead of in delivery conduit 12, such as in patient interface device 14. It should also be understood that exhaust vent 16 can have a wide variety of configurations depending on the desired manner in which gas is to be vented from pressure support system 2.

The present invention also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 14 is a nasal/oral mask. It is to be understood, however, that patient interface 14 can include a nasal mask, nasal pillows, a tracheal tube, an endotracheal tube, or any other device that provides a suitable gas flow communicating function. Also, for purposes of the present invention, the phrase "patient interface" can include delivery conduit 12 and any other structures that couple the source of pressurized breathing gas to patient 10.

In the illustrated embodiment, pressure support system 2 includes a pressure controller in the form of a valve 18 provided in internal delivery conduit 20 provided in a housing of pressure support device 4. Valve 18 controls the pressure of the flow of breathing gas from gas flow generator 6 that is delivered to patient 10. For present purposes, gas flow generator 6 and valve 18 are collectively referred to as a pressure generating system because they act in concert to control the pressure and/or flow of gas delivered to patient 10. However, it should be apparent that other techniques for controlling the pressure of the gas delivered to patient 10, such as varying the blower speed of gas flow generator 6, either alone or in combination with a pressure control valve, are contemplated by the present invention. Thus, valve 18 is optional depending on the technique used to control the pressure of the flow of breathing gas delivered to patient 10. If valve 18 is eliminated, the pressure generating system corresponds to gas flow generator 6 alone, and the pressure of gas in the patient circuit is controlled, for example, by controlling the motor speed of gas flow generator 6.

Pressure support system 2 further includes a flow sensor 22 that measures the flow of the breathing gas within delivery conduit 20 and delivery conduit 12. In the particular embodiment shown in FIG. 1, flow sensor 22 is interposed in line with delivery conduits 20 and 12, most preferably downstream of valve 18. Pressure support system 2 additionally includes a pressure sensor 27 that detects the pressure of the pressurized fluid in delivery conduit 20. While the point at which the flow is measured by flow sensor 22 and the pressure is measured by pressure sensor 27 are illustrated as being within pressure support device 4, it is to be understood that the location at which the actual flow and pressure measurements are taken may be anywhere along delivery conduits 20 or 12. The flow of breathing gas measured by flow sensor 22 and the pressure detected by pressure sensor 27 are provided to processing unit 24 to determine the flow of gas at patient 10 ($Q_{PATIENT}$).

Techniques for calculating $Q_{PATIENT}$ are well known, and take into consideration the pressure drop of the patient circuit, known leaks from the system, i.e., the intentional exhausting of gas from the circuit as indicated by arrow E in FIG. 1, and unknown leaks from the system, such as leaks at the mask/patient interface. The present invention contemplates using any known or hereafter developed technique for calculating leak flow, and using this determination in calculating $Q_{PATIENT}$ using measured flow and pressure. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 10 are contemplated by the present invention, such as, without limitation, measuring the flow directly at patient 10 or at other locations along delivery conduit 12, measuring patient flow based on the operation of gas flow generator 6, and measuring patient flow using a flow sensor upstream of valve 18.

In some non-limiting embodiments of the disclosed concept, pressure support system 2 also includes a proximal pressure sensor 28 that is in fluid communication with a point along delivery conduit 12. For example, without limitation, proximal pressure sensor 28 may be in fluid communication with a point on delivery conduit 12 near patient interface device 14 via a probe connected between proximal pressure sensor 28 and the point on delivery conduit 12. Proximal pressure sensor 28 facilitates measuring pressure proximate the point on delivery conduit 12 and provides the measured proximal pressure to processing unit 24. It will be appreciated that in some exemplary embodiments, proximal pressure sensor 28 may be omitted.

While the flow sensor 22, pressure sensor 27, and proximal pressure sensor 28 have been shown in conjunction with the pressure support system 2 illustrated in FIG. 1, it will be appreciated by those having ordinary skill in the art that other types of sensors may also be employed in conjunction with pressure support system 2 without departing from the scope of the disclosed concept. For example, and without limitation, a temperature sensor may be used to measure temperature, a proximity/contact sensor may be used to sense contact between patient 10 and components of the patient interface. Other types of sensors that may be employed in conjunction with pressure support system include, for example and without limitation, location sensors (e.g, global positioning system sensors) to determine a location of pressure support system 2, light sensors to sense light, an $SpO_2$ sensor (shown in FIG. 2) to detect blood oxygen levels (and to detect reduced $CO_2$ sensitivity (shown in FIG. 2). It will be appreciated that the foregoing examples of types of sensors that may be employed in conjunction with pressure support system 2 is not exhaustive and other types of sensors may also be employed without departing from the scope of the disclosed concept.

Processing unit 24 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 2. Processing unit 24 is structured to receive outputs of one or more sensors structured to gather data related to effectiveness of the pressure support therapy. An example of such sensors is flow sensor 22 and pressure sensor 27. However, other types of sensors may also gather data related to effectiveness of the pressure support therapy and be employed with processing unit 24, as will be described in more detail herein. Processing unit 24 is also structured to analyze outputs of the sensors while pressure support therapy is provided to the patient to determine patient airflow and pressure waveforms in the patient circuit.

An input/output device 26 is provided for setting various parameters used by airway pressure support system 2, as well as for displaying and outputting information and data to a user, such as a patient, clinician or caregiver.

One or both of an audible indicator 31 (e.g., without limitation, a buzzer) and/or a visual indicator 33 (e.g., a flashing light) which may be selectively activated by processing unit 24 may be provided in or on pressure support device 4.

It will be appreciated that pressure support device 4 may include additional components that are not illustrated in the schematic diagram of FIG. 1. For example, without limitation, pressure support device 4 may include a filter to filter breathing gas provided to patient 10 and a humidifier to humidify breathing gas provided to patient 10.

In the illustrated, non-limiting exemplary embodiment of the present invention, airway pressure support system 2 essentially functions as a CPAP pressure support system and pressure support device 4 provides functions of a CPAP base unit. Pressure support system 2, therefore, includes all of the capabilities necessary in such systems in order to provide appropriate CPAP pressure levels to patient 10. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Figure 2:
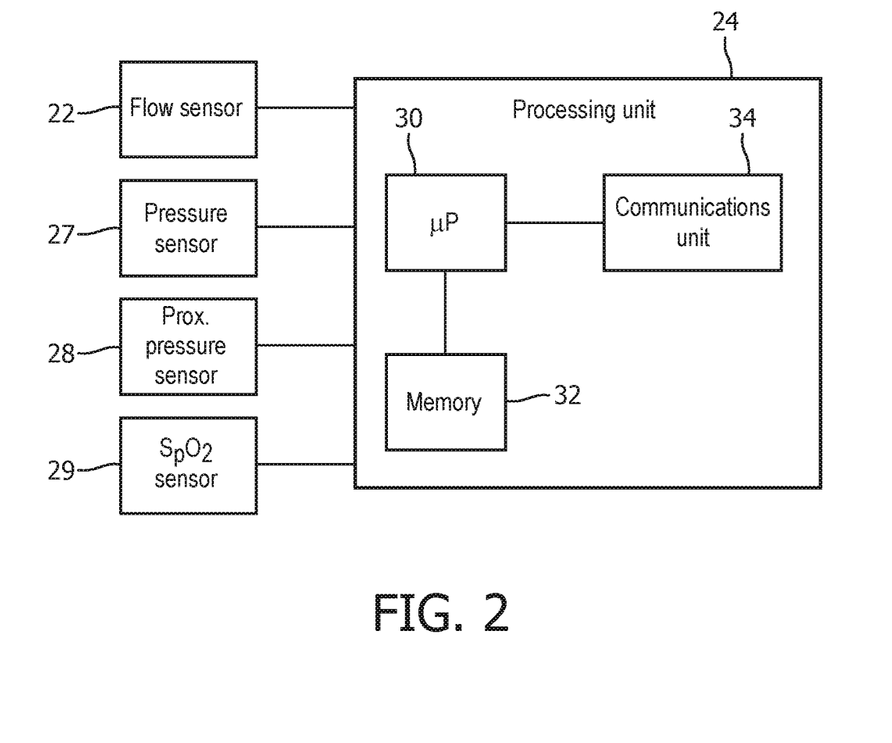
FIG. 2 is a schematic diagram of a processing unit according to an exemplary embodiment of the disclosed concept.

FIG. 2 is a block diagram of processing unit 24 in accordance with a non-limiting exemplary embodiment of the disclosed concept. Processing unit 24 includes a processor 30, a memory 32, and a communication unit 34. Processor 30 may form all or part of a processing portion which may be, for example, a microprocessor, a microcontroller or some other suitable processing device. Memory 32 may form all or part of a memory portion that may be internal to the processing portion or operatively coupled to the processing portion and provide a storage medium for data and software executable by the processing portion for implementing functionality of processing unit 23 and controlling the operation of pressure support system 2. Memory 32 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory.

Communication unit 34 may provide for communication between processing unit 24 and other components of pressure support device 4, components of the patient circuit, or other external devices via the internet, cellular, WiFi, wired telephone line, or any other suitable means. For example, without limitation, communication unit 34 may facilitate communication with various sensors such as flow control sensor 22. Communication unit 34 may also facilitate communication with external devices. For example, without limitation, communication unit 34 may facilitate communication with electronic devices such as a phone, tablet, computer, or other devices whether local or distant, directly or via a network. Communication facilitated by communication unit 34 may allow processing unit 24 to send and/or receive data from the component or device it communicates with.

As previously described, processing unit 24 receives outputs from one or more sensors such as, for example and without limitation, flow sensor 22, pressure sensor 27, and $SpO_2$ sensor 29. Although flow sensor 22, pressure sensor 27, and $SpO_2$ sensor 29 are shown, it will be appreciated that one or more of these sensors may be omitted without departing from the scope of the disclosed concept. It will also be appreciated that processing unit 24 may receive outputs from one or more other types of sensors that are not shown in FIG. 2. For example, without limitation, processing unit 24 may receive outputs from one or more of a temperature sensor, a proximity/contact sensor, location sensors, microphones, or identification sensors.

Figure 3:
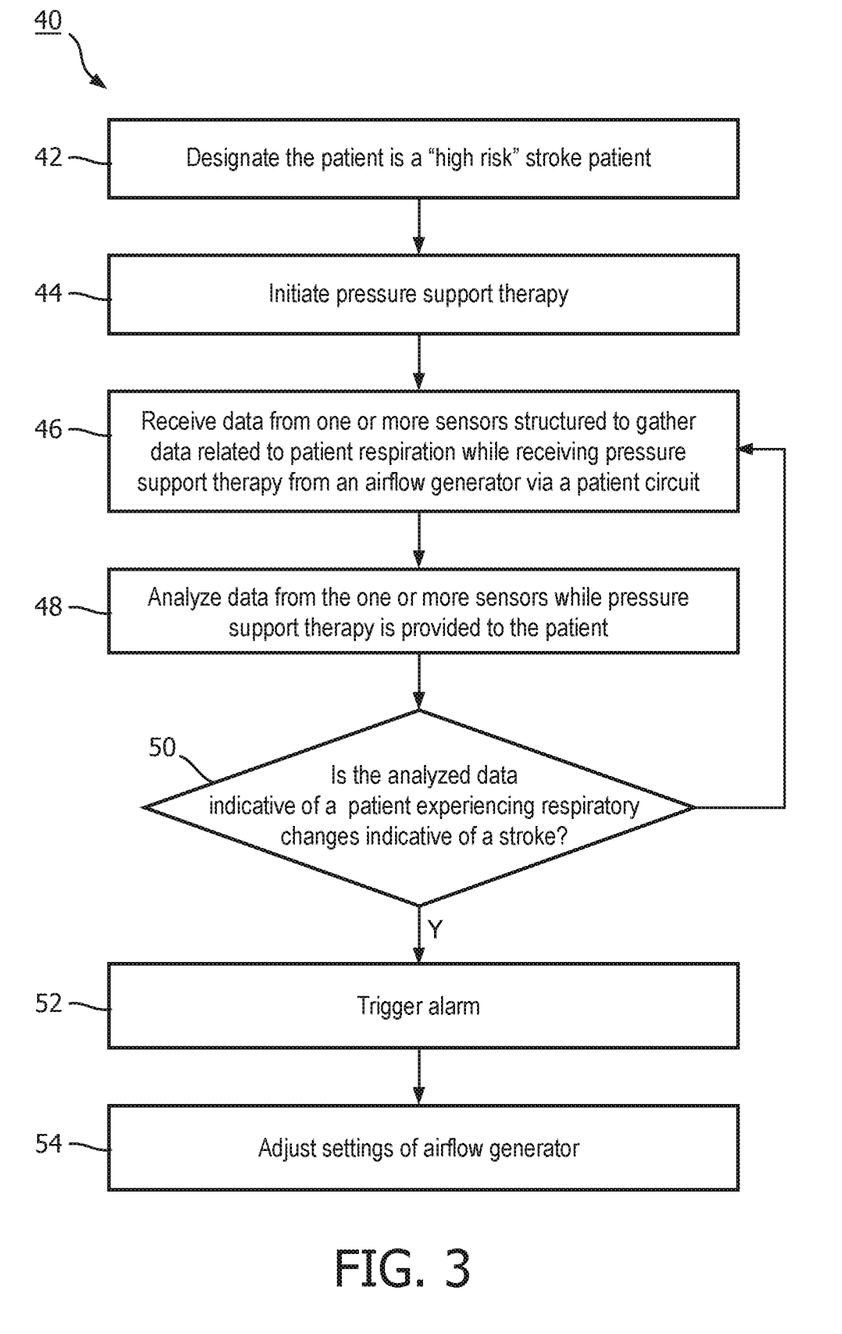
FIG. 3 is a flowchart of a method of detecting stroke in a patient receiving a pressure support therapy according to an exemplary embodiment of the disclosed concept.

FIG. 3 is a flowchart of a method 40 of detecting stroke in a patient receiving a pressure support therapy. The method of FIG. 3 may be employed in, for example, pressure support system 2. As an initial step, such as shown at 42, the patient is designated as a "high risk" stroke patient. Some of the respiratory changes associated with stroke are also associated with other disorders (e.g. Cheyne-Stokes Respiration is also associated with chronic heart failure) so it is helpful to designate the patient as being at high risk for stroke to avoid misinterpretation of respiratory changes and excessive false-positive stroke alarms. Such identification could be done, for example, by a physician prescribing the patient a special PAP device for stroke patients or by engaging a special stroke detection mode on the patient's PAP device. Patients could be designated as being at high risk for stroke based on a combination of risk factors including: personal history of stroke, family history of stroke, age, race, gender, blood pressure, history of smoking, atherosclerosis, atrial fibrillation, blood cholesterol levels, diet, obesity, lifestyle (physical activity), geographic location (e.g. stroke belt states), and history of drug or alcohol abuse.

Next, at some point after designating the patient is a "high risk" stroke patient, pressure support therapy is initiated, such as shown at 44. Such therapy may be provided via any suitable system for administering PAP (e.g., without limitation, DreamStation PAP from Philips Respironics). Such therapy may be initiated by the patient, a caregiver, or any other person or persons assisting the patient.

Next at 46, while the patient is undergoing pressure support therapy, data is received from one or more sensors which are structured to gather data related to patient respiration while receiving pressure support therapy from an airflow generator via a patient circuit. Such data includes patient airflow, such as obtained by flow sensor 22 of FIG. 1, and pressure waveforms, such as obtained by pressure sensor 27 of FIG. 1. Data from other sensors, for example, without limitation, $SpO_2$ sensor 29 of FIG. 2, may also be obtained regarding operation of the PAP device and/or condition of the patient.

Next at 48, data from the one or more sensors is analyzed while pressure support therapy is provided to the patient. Such analysis may include analyzing patient airflow and pressure waveforms. If at 50, it is then determined that the analyzed data is indicative of a patient experiencing respiratory changes indicative of a stroke, then an alarm is triggered. As previously discussed in the background section, when a stroke occurs, specific respiratory changes may occur depending on the region(s) of the brain affected by the stroke lesions. Possible respiratory changes include:

a. Acute respiratory failure
 b. Central Hypoventilation Syndrome (Ondine's Curse)
 c. Emergence/exacerbation of OSA, CSA, and Cheyne-Stokes Respiration
 d. Neurogenic Hyperventilation
 e. Reduced $CO_2$ sensitivity
 f. Apneustic Breathing
 g. Ataxic Respiration
 h. Intractable Hiccups Hence, if the analyzed data indicates that a patient is experiencing any of the preceding respiratory changes, the patient may be experiencing a stroke and thus one or more alarms is/are triggered, such as shown at 52. It is to be appreciated that recognition of such respiratory changes from patient airflow and pressure waveforms may be readily accomplished via known and/or readily available means. In example embodiments of the present invention each of these conditions is correlated with specific characteristics in the patient's flow and/or pressure waveforms. As an example, Apneustic Breathing is characterized by a pause in airflow during or just after inhalation. This would be detectable by analyzing the signal from flow sensor 22.

One or more of a variety of alarms may be triggered at 52. Such alarm or alarms may be audible, visual, or a combination thereof and may be produced on or by the pressure support device (e.g., without limitation, via audible indicator 31 and/or visual indicator 33) which is providing the pressure support therapy (e.g., without limitation, via one or more speakers, light sources, display screens, etc.) or via another device, local to or remote from the patient. In one example embodiment of the present invention, triggering an alarm comprises sending an automated message (e.g., without limitation, via text or e-mail) to at least one of a physician or a caregiver. In another example embodiment of the present invention, triggering an alarm comprises alerting emergency services (e.g., via a wired or wireless phone call or other suitable notification). It is to be appreciated that such examples of triggered alarms are provided for exemplary purposes only and that other alarms or combinations of alarms may be utilized without varying from the scope of the present invention.

In addition to triggering an alarm, upon determining that the analyzed data is indicative of a patient experiencing respiratory changes indicative of a stroke, the settings of the airflow generator may be adjusted. For example, a back-up ventilation mode may be engaged, such as shown at 54, which provides the patient with ventilation until emergency personnel arrive. In an example embodiment of the present invention, the back-up ventilation mode adjusts the output of the airflow generator (i.e. pressure and flow) to ensure that physiologically appropriate (i.e. life-sustaining) ventilation (i.e. tidal volume and minute ventilation) are maintained. Such modes are commonly referred to as "mandatory ventilation" since the device attempts to drive the required patient airflow regardless of the contribution of the patient.

If at 50, it is determined that the analyzed data is not indicative of a patient experiencing respiratory changes indicative of a stroke, then the method returns to 46 wherein further data is received. The method thus generally continues to repeat 46, 48 and 50 until either it is determined that the analyzed data is indicative of a patient experiencing respiratory changes indicative of a stroke or delivery of the pressure support therapy has ceased.

From the foregoing it is thus to be appreciated that embodiments of the present invention provide a means to detect the likely occurrence of a stroke and alert necessary personnel of such occurrence. Embodiments of the present invention also can provide initial treatment of stroke symptoms until such personnel arrive at the patient.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A method of detecting stroke in a patient receiving a pressure support therapy, the method comprising:
 receiving data from one or more sensors structured to gather data related to patient respiration while the patient is receiving the pressure support therapy from an airflow generator via a patient circuit;
 analyzing the data from the one or more sensors while the pressure support therapy is provided to the patient;
 determining by analyzing patient airflow and pressure waveforms that the analyzed data from the one or more sensors is indicative of a patient experiencing respiratory changes indicative of a stroke by detecting at least one of acute respiratory failure, emergence/exacerbation of at least one of OSA and Cheyne-Stokes Respiration, neurogenic hyperventilation, reduced $CO_2$ sensitivity, apneustic breathing, ataxic respiration, and intractable hiccups; and
 responsive to said determining, triggering at least one alarm and adjusting settings of the airflow generator.

2. The method of claim 1, wherein the one or more sensors comprise a pressure sensor and a flow sensor.

3. The method of claim 1, further comprising determining the patient is a high risk stroke patient prior to the receiving the data from the one or more sensors.

4. The method of claim 1, wherein the adjusting settings of the airflow generator comprises adjusting settings of the airflow generator to provide mandatory life-sustaining ventilation of the patient.

5. The method of claim 1, wherein the triggering at least one alarm comprises triggering an audible alarm.

6. The method of claim 1, wherein the triggering at least one alarm comprises triggering a visual alarm.

7. The method of claim 1, wherein the triggering at least one alarm comprises sending an automated message to at least one of a physician or a caregiver.

8. The method of claim 1, wherein the triggering at least one alarm comprises alerting emergency services.

9. A pressure support device for providing pressure support therapy to a patient, the pressure support device comprising:
   an airflow generator structured to generate pressure to provide pressure compensation to the patient via a patient circuit;
   one or more sensors comprising a pressure sensor and a flow sensor structured to gather data related to effectiveness of the pressure compensation; and
   a processing unit programmed to:
      receive data from the sensors while the patient is receiving the pressure support therapy from the airflow generator via the patient circuit;
      analyze the data from the sensors while the pressure support therapy is provided to the patient;
      determine by analyzing patient airflow and pressure waveforms that the analyzed data from the sensors is indicative of a patient experiencing respiratory changes indicative of a stroke by detecting at least one of acute respiratory failure, emergence/exacerbation of at least one of OSA and Cheyne-Stokes Respiration, neurogenic hyperventilation, reduced $CO_2$ sensitivity, apneustic breathing, ataxic respiration, and intractable hiccups; and
      responsive to said determining, trigger at least one alarm and adjust settings of the airflow generator.

10. The pressure support device of claim 9, further comprising an audible indicator and wherein the processing unit is programmed to activate the audible indicator as the triggering of the at least one alarm responsive to said determining.

11. The pressure support device of claim 9, further comprising a visual indicator and wherein the processing unit is programmed to activate the visual indicator as the triggering of the at least one alarm responsive to said determining.

* * * * *